United States Patent
Kanaya

(10) Patent No.: US 11,881,881 B2
(45) Date of Patent: Jan. 23, 2024

(54) DETERMINATION APPARATUS, BIOMAGNETISM MEASURING APPARATUS, AND DETERMINATION METHOD

(71) Applicant: Mitsuhisa Kanaya, Tokyo (JP)

(72) Inventor: Mitsuhisa Kanaya, Tokyo (JP)

(73) Assignee: RICOH COMPANY, LTD., Tokyo (JP)

(*) Notice: Subject to any disclaimer, the term of this patent is extended or adjusted under 35 U.S.C. 154(b) by 594 days.

(21) Appl. No.: 17/103,973

(22) Filed: Nov. 25, 2020

(65) Prior Publication Data

US 2021/0161474 A1 Jun. 3, 2021

(30) Foreign Application Priority Data

Nov. 28, 2019 (JP) ................ 2019-215317
Sep. 25, 2020 (JP) ................ 2020-161314

(51) Int. Cl.
*H04B 1/10* (2006.01)
*H04B 15/00* (2006.01)
(Continued)

(52) U.S. Cl.
CPC .......... *H04B 1/10* (2013.01); *H04B 1/126* (2013.01); *H04B 15/00* (2013.01); *H04B 15/02* (2013.01); *A61B 5/4094* (2013.01); *A61B 5/7214* (2013.01)

(58) Field of Classification Search
CPC ........ H04B 1/10; H04B 1/1027; H04B 1/126; H04B 15/02; H05B 15/00; A61B 5/00; A61B 5/7203; A61B 5/7214; A61B 5/742; A61B 5/4094; A61B 5/0048; G01R 33/0029; G01R 33/0035; G01R 33/10; G01R 33/12
See application file for complete search history.

(56) References Cited

U.S. PATENT DOCUMENTS

| 8,754,640 | B2 * | 6/2014 | Vig | ............... G01R 33/0035 324/202 |
| 9,636,019 | B2 * | 5/2017 | Hendler | ............... A61B 5/0055 |

(Continued)

FOREIGN PATENT DOCUMENTS

| JP | 2009-188455 | 8/2009 |
| JP | 2019-013284 | 1/2019 |

OTHER PUBLICATIONS

Kensuke Sekihara, et al.,"Dual signal subspace projection (DSSP): A novel algorithm for removing large interference in biomagnetic measurements" HHS Public Access Author manuscript J Neural Eng. Author manuscript; available in PMC Dec. 10, 2018.p. 1-43.

(Continued)

*Primary Examiner* — Quochien B Vuong
(74) *Attorney, Agent, or Firm* — XSENSUS LLP

(57) ABSTRACT

A determination apparatus includes circuitry configured to: compare signal separation results obtained by a plurality of signal separation algorithms executed on a mixed signal in which signals emitted from a plurality of signal sources are mixed, each of the plurality of signal separation algorithms being an algorithm separating a signal of interest from the mixed signal; and determine a parameter of each of the plurality of signal separation algorithms based on a comparison result.

12 Claims, 5 Drawing Sheets

(51) Int. Cl.
*A61B 5/05* (2021.01)
*H04B 15/02* (2006.01)
*H04B 1/12* (2006.01)
*A61B 5/00* (2006.01)

(56) References Cited

U.S. PATENT DOCUMENTS

| 9,642,554 | B2* | 5/2017 | Simola | A61B 5/4064 |
| 10,985,846 | B2* | 4/2021 | Shibahara | H04B 10/11 |
| 2019/0000389 | A1 | 1/2019 | Hikida | |

OTHER PUBLICATIONS

Samu Taulu, et al., "Spatiotemporal signal space separation method for rejecting nearby interference in MEG measurements" Phys. Med. Biol. 51 (2006) p. 1-p. 10.

* cited by examiner

DETERMINATION APPARATUS, BIOMAGNETISM MEASURING APPARATUS, AND DETERMINATION METHOD

CROSS-REFERENCE TO RELATED APPLICATIONS

This patent application is based on and claims priority under 35 U.S.C. § 119(a) to Japanese Patent Application Nos. 2019-215317, filed on Nov. 28, 2019, and 2020-161314, filed on Sep. 25, 2020 in the Japan Patent Office, the entire disclosures of which are incorporated herein by reference.

BACKGROUND

Technical Field

The present disclosure relates to a determination apparatus, a biomagnetism measuring apparatus, and a determination method.

Related Art

In biomagnetism measurement, interference magnetic field signals (artifacts) generated due to an environmental magnetic field such as geomagnetism or a measurement action itself is very large. The interference magnetic field signals are major obstacles to acquisition of accurate measurement data. Therefore, removal of the interference magnetic field signals (noise removal) is a major issue.

As a technique of removing the interference magnetic field signals, a technique of covering a measuring apparatus with a magnetic shield is known, such as a magnetic shield room. Further, as another technique of removing the interference magnetic field signals, a technique of performing certain signal processing on the measured signal to extract a signal of interest is known.

When removing the interference magnetic field signals by the signal processing (extracting signals of interest by separation), many parameters are to be determined for a signal separation algorithm. Therefore, in order to obtain a sufficient effect, experts have to manually adjust the parameters.

To address the above issue, a method is proposed of automatically deriving optimal parameters. Specifically, when the signal of interest is extracted by separation, characteristic spike waves are detected from the extracted signals, and an equivalent current dipole (ECD) estimation (dipole estimation) is performed. Based on an evaluation result obtained by the ECD estimation (dipole estimation), the optimal parameters are automatically derived, and the interference magnetic field signals are removed using the derived optimal parameters.

SUMMARY

According to an embodiment, a determination apparatus includes circuitry configured to: compare signal separation results obtained by a plurality of signal separation algorithms executed on a mixed signal in which signals emitted from a plurality of signal sources are mixed, each of the plurality of signal separation algorithms being an algorithm separating a signal of interest from the mixed signal; and determine a parameter of each of the plurality of signal separation algorithms based on a comparison result.

BRIEF DESCRIPTION OF THE DRAWINGS

A more complete appreciation of the disclosure and many of the attendant advantages and features thereof can be readily obtained and understood from the following detailed description with reference to the accompanying drawings, wherein.

Figure 1:
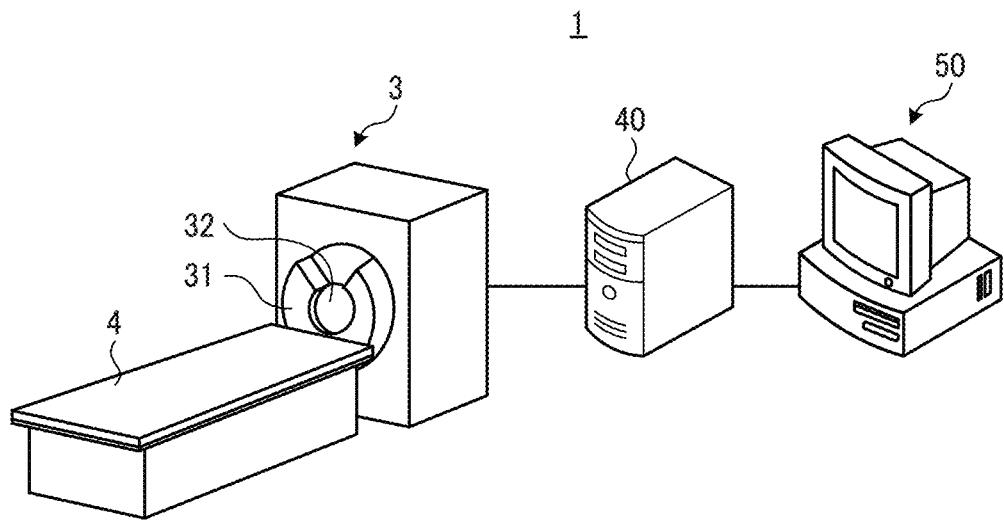
FIG. 1 is a schematic diagram illustrating a biomedical signal measuring system, according to a first embodiment of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

First Embodiment

A determination apparatus, a biomagnetism measuring apparatus, and a determination method according to an embodiment of the present disclosure are described hereinafter in detail with reference to the drawings. The present disclosure, however, is not limited to the following embodiment, and the constituent elements of the following embodiment include elements that can be easily conceived by those skilled in the art, those being substantially the same ones, and those being within equivalent ranges. Furthermore, various omissions, substitutions, changes, and combinations of the constituent elements can be made without departing from the gist of the following embodiments.

Schematic Configuration of Biomedical Signal Measuring System

FIG. 1 is a schematic diagram illustrating a biomedical signal measuring system 1, according to a first embodiment. A schematic configuration of the biomedical signal measuring system 1 according to the present embodiment is described with reference to FIG. 1.

The biomedical signal measuring system 1 measures a plurality of types of biomedical signals of a subject, such as magneto-encephalography (MEG) signals and electro-encephalography (EEG) signals, and displays such measured signals. The biomedical signals to be measured are not limited to the MEG signals and the EEG signals. Other examples of signals to be measured by the biomedical signal measuring system 1 include, other signals relating to brain activity, and signals obtained by measuring a magnetic field caused by activities of other parts such as a spine, heart, or muscle.

As illustrated in FIG. 1, the biomedical signal measuring system 1 includes a measuring apparatus 3, a server apparatus 40, and an information processing apparatus 50. The measuring apparatus 3 measures one or more biomedical signals of the subject. The server apparatus 40 records the biomedical signals measured by the measuring apparatus 3. The information processing apparatus 50 analyzes the biomedical signals recorded in the server apparatus 40. In the present embodiment, as illustrated in FIG. 1, the server apparatus 40 and the information processing apparatus 50 are provided as separate units. However, no limitation is indicated thereby. For example, at least a part of functions of the server apparatus 40 may be implemented by the information processing apparatus 50. The information processing apparatus 50 is an example of a determination apparatus and a biomagnetism measuring apparatus.

In the present embodiment, as illustrated in FIG. 1, the subject lies on a table 4 with electrodes (or sensors) for EEG measurement attached to his or her head, and puts his or her head in a hollow 32 of a Dewar 31 of the measuring apparatus 3. The Dewar 31 is a container of liquid helium that can be used at very low temperatures. A number of magnetic sensors for MEG measurement are disposed on the inner surface of the hollow 32 of Dewar 31. The measuring apparatus 3 collects the EEG signals and MEG signals through the electrodes and the magnetic sensors, respectively. Further, the measuring apparatus 3 outputs data including the collected EEG signals and MEG signals to the server apparatus 40. Note that such collected EEG signals and MEG signals may be hereinafter referred to as "measurement data". The measurement data output to the server apparatus 40 is read to and is displayed and analyzed by the information processing apparatus 50. As known in the art, the Dewar 31 equipped with magnetic sensors and the table 4 are provided inside a magnetically shielded room. However, illustration of the magnetically shielded room is omitted in FIG. 1, in order to simplify the drawing.

The information processing apparatus 50 displays waveforms of the MEG signals from the plurality of magnetic sensors and waveforms of the EEG signals from the plurality of electrodes in synchronization with each other on the same time axis. The EEG signals indicate an inter-electrode voltage value obtained for electrical activities of nerve cells (i.e., a flow of ionic charge caused at dendrites of neurons at the time of synaptic transmission). The MEG signals indicate minute fluctuations in the magnetic field caused by electrical activities of a brain. The magnetic field that is generated by the brain is detected by a high-sensitivity superconducting quantum interference device (SQUID) sensor. The MEG signals and the EEG signals are examples of "biomedical signals". The MEG signals are an example of "biomagnetism measurement signals".

Hardware Configuration of Information Processing Apparatus

Figure 2:
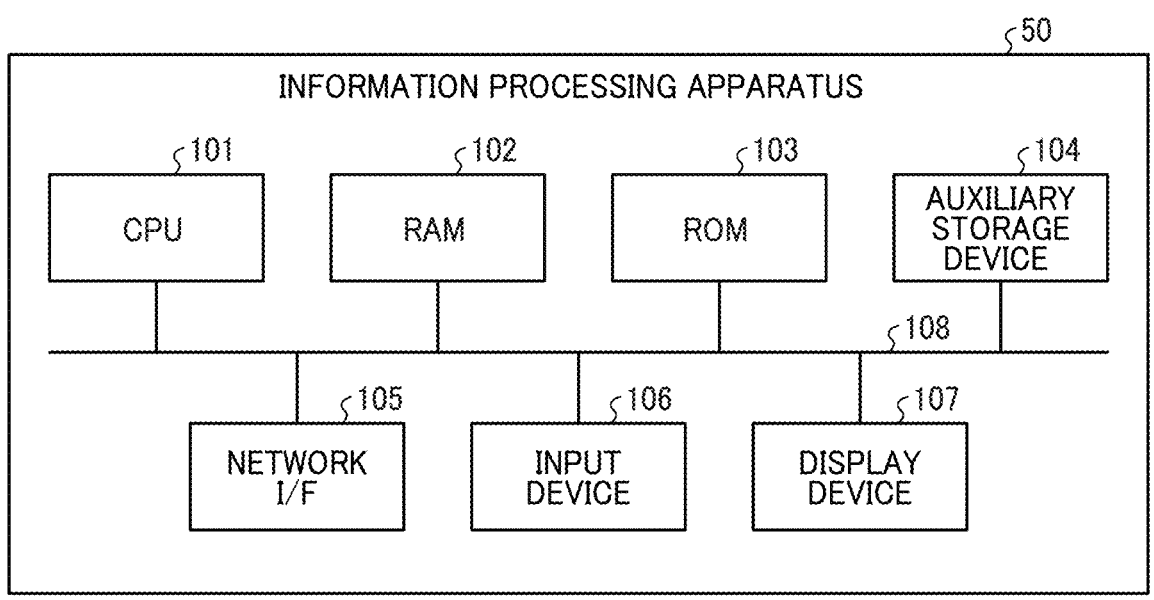
FIG. 2 is a block diagram illustrating an example of a hardware configuration of an information processing apparatus, according to the first embodiment of the present disclosure.

FIG. 2 is a block diagram illustrating an example of a hardware configuration of an information processing apparatus 50, according to the first embodiment. A hardware configuration of the information processing apparatus 50 according to the present embodiment is described with reference to FIG. 2.

As illustrated in FIG. 2, the information processing apparatus 50 includes a central processing unit (CPU) 101, a random access memory (RAM) 102, a read only memory (ROM) 103, an auxiliary storage device 104, a network interface (I/F) 105, an input device 106, and a display device 107. These hardware resources are connected to each other through a bus 108.

The CPU 101 is a processor that controls overall operation of the information processing apparatus 50, and performs various kinds of information processing. The CPU 101 executes an information display program stored in the ROM 103 or the auxiliary storage device 104, to control display operation of a measurement collection screen and an analysis screen such as a time-frequency analysis screen.

The RAM 102 is a volatile storage device to store main control parameters and information. The RAM 102 is used as a work area for the CPU 101. The ROM 103 is a non-volatile storage device to store a program such as a basic input/output program. For example, the above-described information display program may be stored in the ROM 103.

The auxiliary storage device 104 is a storage device such as a hard disk drive (HDD) or a solid state drive (SSD). The auxiliary storage device 104 stores, for example, a control program to control operation of the information processing apparatus 50, various kinds of data and files required for operation of the information processing apparatus 50.

The network I/F 105 is a communication interface through which the information processing apparatus 50 communicates with apparatuses or devices on a network, such as the server apparatus 40. For example, the network I/F 105 is implemented by a network interface card (NIC) compliant with the transmission control protocol (TCP)/Internet protocol (IP).

The input device 106 is a user interface device having input functions. Examples of the input device 106 include, but are not limited to, a touch panel, a keyboard, a mouse, and operation keys. The display device 107 is a device that displays various kinds of information. The display device 107 is implemented by, for example, a display function of the touch panel, a liquid crystal display (LCD), or an organic electroluminescence (EL). The display device 107 displays the measurement collection screen and the analysis screen, and updates the screens in response to input and output operation through the input device 106.

The hardware configuration of the information processing apparatus 50 illustrated in FIG. 2 is just one example, and the information processing apparatus can further include any suitable hardware components. Although the description given above is of an example in which the information processing apparatus 50 is implemented by a personal computer (PC) having the hardware configuration as illustrated in FIG. 2, the information processing apparatus can by any other suitable apparatus or device such as a mobile terminal such as a tablet PC. In this case, the network I/F 105 can be implemented by a communication interface having a wireless communication capability.

Functional Configuration of Information Processing Apparatus

Figure 3:
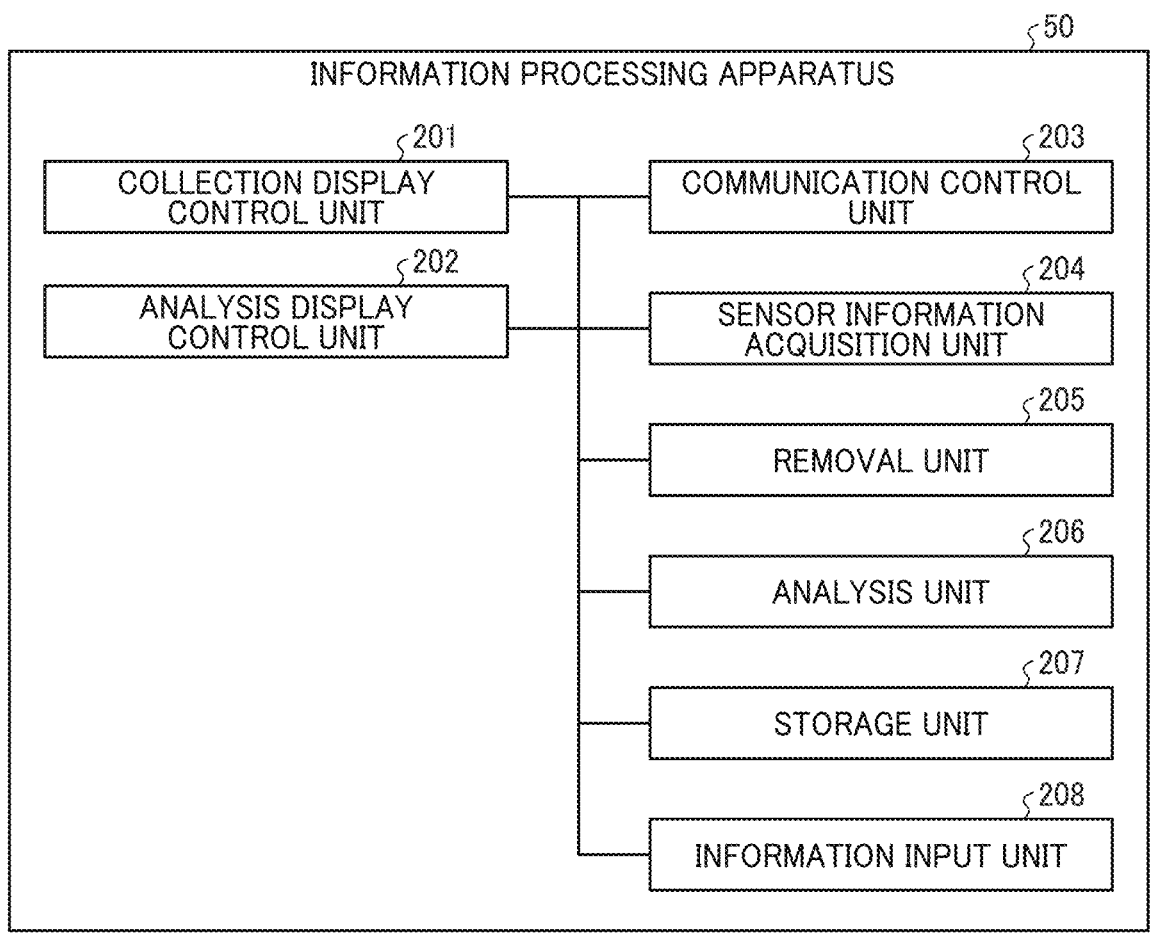
FIG. 3 is a block diagram illustrating an example of a functional configuration of the information processing apparatus, according to the first embodiment of the present disclosure.

FIG. 3 is a block diagram illustrating an example of a functional configuration of the information processing apparatus 50, according to the present embodiment. A functional configuration of the information processing apparatus 50 according to the present embodiment is described with reference to FIG. 3.

As illustrated in FIG. 3, the information processing apparatus 50 includes a collection display control unit 201, an analysis display control unit 202, a communication control unit 203, and a sensor information acquisition unit 204. The information processing apparatus 50 further includes a removal unit 205, an analysis unit 206, a storage unit 207, and an information input unit 208. The removal unit 205 is an example of a determination apparatus and a determination unit.

The collection display control unit 201 controls a screen display when data output from the sensors are being collected.

The analysis display control unit 202 controls a screen display of, for example, the signal strength of the biomedical signals computed and obtained by the analysis unit 206 based on the sensor data (EEG signals or MEG signals) acquired by the sensor information acquisition unit 204. The analysis display control unit 202 controls, for example, a heat map display, a three-dimensional image display, a cross-sectional image display, and a reproduction display.

The communication control unit 203 communicates data with, for example, the measuring apparatus 3 or the server apparatus 40. The communication control unit 203 is implemented by the network I/F 105 illustrated in FIG. 2.

The sensor information acquisition unit 204 acquires sensor data (EEG signals or MEG signals) from the measuring apparatus 3 or the server apparatus 40 through the communication control unit 203.

The removal unit 205 uses a signal separation algorithm (removal algorithm) to generate signals obtained by removing interference magnetic field signals (interference signals) from biomagnetism measurement signals measured by a plurality of sensors. The biomagnetism measurement signals are time-series sensor signals of multiple channel. The removal algorithm is an algorithm that removes the interference signals from the biomagnetism measurement signals, to extract the sensor signals from which the interference signals are removed as signals of interest.

The removal unit 205 performs a plurality of removal algorithms on the biomagnetism measurement signals (MEG signals), to obtain a plurality of signal separation results corresponding to the plurality of removal algorithms. Further, the removal unit 205 compares the plurality of signal separation results corresponding to the plurality of removal algorithms performed on the biomagnetism measurement signals, to determine a parameter for each of the plurality of signal separation algorithms. The removal unit 205 outputs each determined parameter as an optimal parameter of each of the plurality of signal separation algorithms.

The analysis unit 206 analyzes the sensor signals from which the interference magnetic field signals are removed by the removal unit 205, to compute a signal indicating the signal strength in each part of the brain.

The storage unit 207 stores data such as the sensor signals from which the interference magnetic field signals are removed by the removal unit 205, and the signal indicating the signal strength computed by the analysis unit 206. The storage unit 207 is implemented by the RAM 102 or the auxiliary storage device 104 illustrated in FIG. 2.

The information input unit 208 receives an input operation of annotation information for adding related information as an annotation to the sensor information, and various input operations for a time-frequency analysis screen 601. The information input unit 208 is implemented by the input device 106 as illustrated in FIG. 2.

The collection display control unit 201, the analysis display control unit 202, the sensor information acquisition unit 204, the removal unit 205, and the analysis unit 206 are implemented by the CPU 101 executing the program read from the ROM 103 or the like and developed on the RAM 102. A part or all of the collection display control unit 201, the analysis display control unit 202, the sensor information acquisition unit 204, the removal unit 205, and the analysis unit 206 can be implemented by hardware circuitry such as an application specific integrated circuit (ASIC) or a field-programmable gate array (FPGA), in place of a software program.

Further, the functional units illustrated in FIG. 3 conceptually represent functions and not limited to those illustrated in FIG. 3. For example, a plurality of functional units that are independent from each other in FIG. 3 can be combined into one functional unit. Alternatively, one of the plurality of functional units illustrated in FIG. 3 may be divided into a plurality of functional units.

Configuration of Removal Unit

Figure 4:
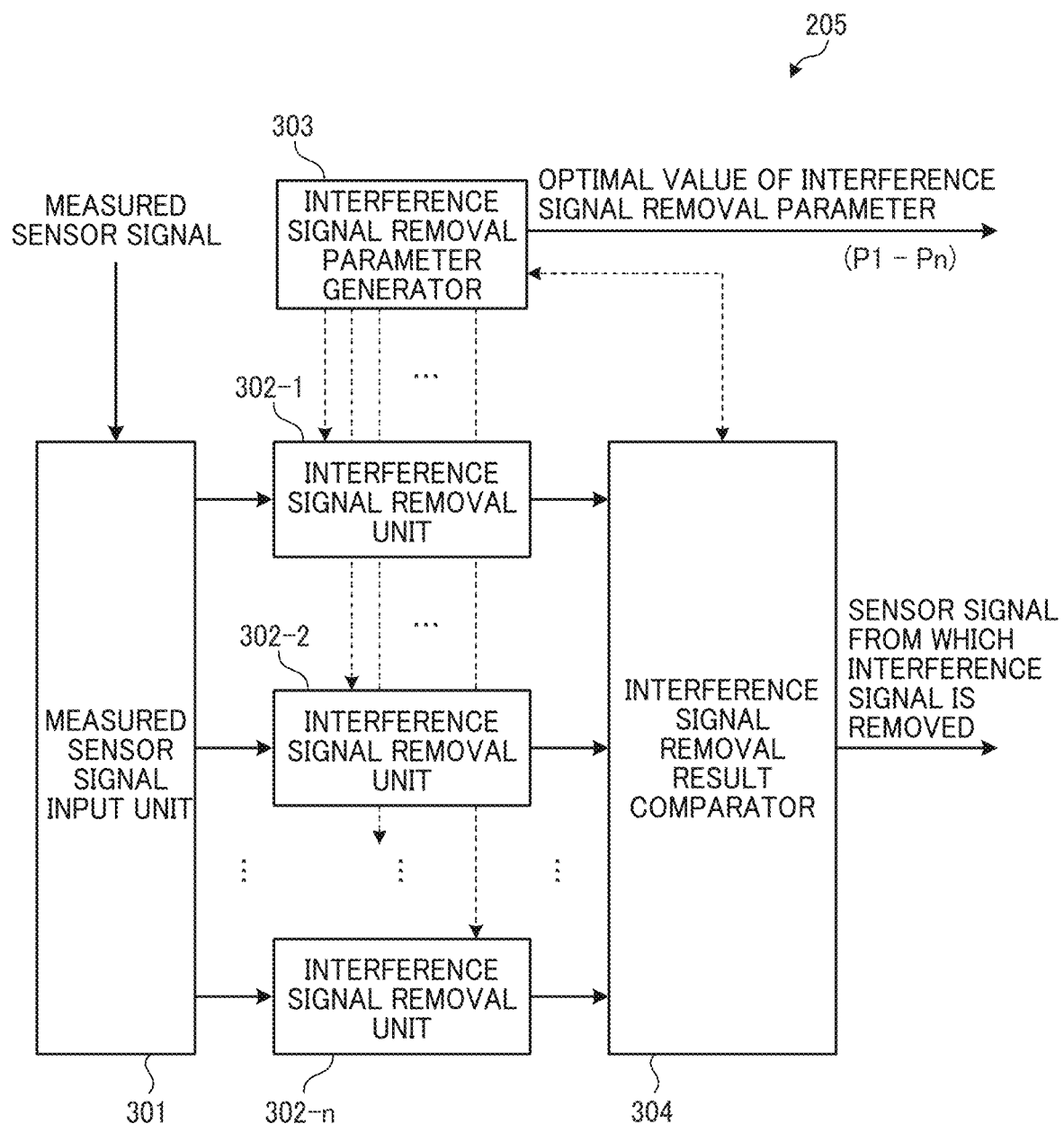
FIG. 4 is a block diagram illustrating an example of a functional configuration of a removal unit illustrated in FIG. 3.

A functional configuration of the removal unit 205 according to the present embodiment is described with reference to FIG. 4. FIG. 4 is a block diagram illustrating an example of a functional configuration of the removal unit 205 illustrated in FIG. 3.

As illustrated in FIG. 4, the removal unit 205 includes a measurement signal input unit 301, an interference signal removal units 302-1 to 302-n, an interference signal removal parameter generator 303, and an interference signal removal result comparator 304 (determination unit). The interference signal removal units 302-1 to 302-n are an example of a plurality of signal separation unit. The interference signal removal parameter generator 303 is an example of a generation unit. The interference signal removal result comparator 304 is an example of determining unit. The removal unit 205 has the plurality of interference signal removal units 302-1 to 302-n that operate based on different removal algorithms respectively.

The measurement signal input unit 301 receives input of time-series sensor signals of multiple channels from extraneous sources, distributes (copies) the input signals, and sends the copied input signals to each of the interference signal removal unit 302-1 to 302-n. The time-series sensor signals of multiple channels are an example of measured sensor signals.

The interference signal removal units 302-1 to 302-n removes the interference signals from the measured sensor signals by using any of the plurality of removal algorithms. The interference signal removal units 302-1 to 302-n operate based on different removal algorithms respectively, and remove the interference signals from the measured sensor signals.

The interference signal removal units 302-1 to 302-$n$ perform signal separation using a parameter corresponding to the removal algorithm to be used among parameters generated by the interference signal removal parameter generator 303, to remove the interference signals from the sensor signals. The interference signal removal unit 302-1 to 302-$n$ send the signals from which the interference signals are removed to the interference signal removal result comparator 304. The interference signal removal unit 302-1 to 302-$n$ performs such interference signal removal processing a plurality of times while the parameters generated by the interference signal removal parameter generator 303 are sent.

The interference signal removal parameter generator 303 generates parameters unique to the plurality of removal algorithms used by the interference signal removal units 302-1 to 302-$n$. The interference signal removal parameter generator 303 sends the generated parameters to the interference signal removal units 302-1 to 302-$n$.

The parameters sent by the interference signal removal parameter generator 303 to the interference signal removal units 302-1 to 302-$n$ are different from each other since the parameter depends on the removal algorithm. Further, the interference signal removal parameter generator 303 may send a set of a plurality of parameters to any one of the interference signal removal units 302-1 to 302-$n$.

The interference signal removal parameter generator 303 repeatedly performs the parameter generation process a plurality of times while changing a value of the parameter according to an instruction from the interference signal removal result comparator 304. For example, the interference signal removal parameter generator 303 has a default value of the parameter of each removal algorithm as a data set. In response to receiving an instruction of the parameter generation process from the interference signal removal result comparator 304, the interference signal removal parameter generator 303 changes each parameter according to a preset rule.

The interference signal removal result comparator 304 receives the sensor signals from which the interference signals are removed by the interference signal removal units 302-1 to 302-$n$, i.e., interference signal removal results. Further, interference signal removal result comparator 304 compares the received sensor signals, to determine the parameter of each of the plurality of removal algorithms.

The interference signal removal result comparator 304 determines whether the sensor signals from which the interference signals are removed are within a predetermined error range. The predetermined error range is set in advance. For example, the predetermined error range is set according to an analysis performance of the analysis unit 206. Note that the predetermined error range may be set and changed based on a result of the interference signal removal process performed in the past.

When the sensor signals from which the interference signals are removed are within the predetermined error range, the interference signal removal result comparator 304 determines the parameter of each of the plurality of removal algorithms used in this interference signal removal process as the parameter of each the plurality of removal algorithms. When the sensor signals from which the interference signals are removed are within the predetermined error range, the interference signal removal result comparator 304 outputs each of these signal separation results to the analysis unit 206.

By contrast, when the sensor signals from which the interference signals are removed are out of the predetermined error range, the interference signal removal result comparator 304 instructs the interference signal removal parameter generator 303 to generate a parameter of each of the plurality of removal algorithms and output each generated parameter to each of the interference signal removal units 302-1 to 302-$n$. Thereby, the interference signal removal result comparator 304 causes the interference signal removal units 302-1 to 302-$n$ to perform the interference signal removal process again, to receive an updated interference signal removal result.

The interference signal removal result comparator 304 repeatedly performs this comparison process until each interference signal removal result is within the predetermined error range. Further, the interference signal removal result comparator 304 eventually outputs, to extraneous sources, the interference signal removal result that is within the predetermined error range and the parameters P1 to Pn used by the interference signal removal units 302-1 to 302-$n$ in the interference signal removal process resulting in the interference signal removal result that is within the predetermined error range.

Example of Removal Algorithm

The removal algorithms used in the interference signal removal units 302-1 to 302-$n$ are selected so that the changes in the removal result due to the changes of the parameter appear as a different series. For example, as the removal algorithms, a combination of the DSSP method (see, for example, K. Sekihara, Y. Kawabata, S. Ushio, S. Sumiya, S. Kawabata, Y. Adachi, and S. S. Nagarajan, "Dual signal subspace projection (DSSP): a novel algorithm for removing large interference in biomagnetic measurements", Journal of Neural Engineering, vol.13, no.3, 036007, 2016) and the TSSP method (see, for example, JP-2019-013284-A) is selected. In addition to or in alternative, as the removal algorithm, the tSSS method (see, for example, S. Taulu, J. Simola, "Spatiotemporal signal space separation method for rejecting nearby interference in MEG measurements", PHYSICS IN MEDICINE AND BIOLOGY, vol.51, 2006, 1759-1768.), or principal component analysis (PCA)/independent component analysis (ICA) may be applied. Further, the removal algorithms are appropriately selected in substantially the same manner in a configuration having three or more interference signal removal units.

Example of Removal Result

Figure 5:
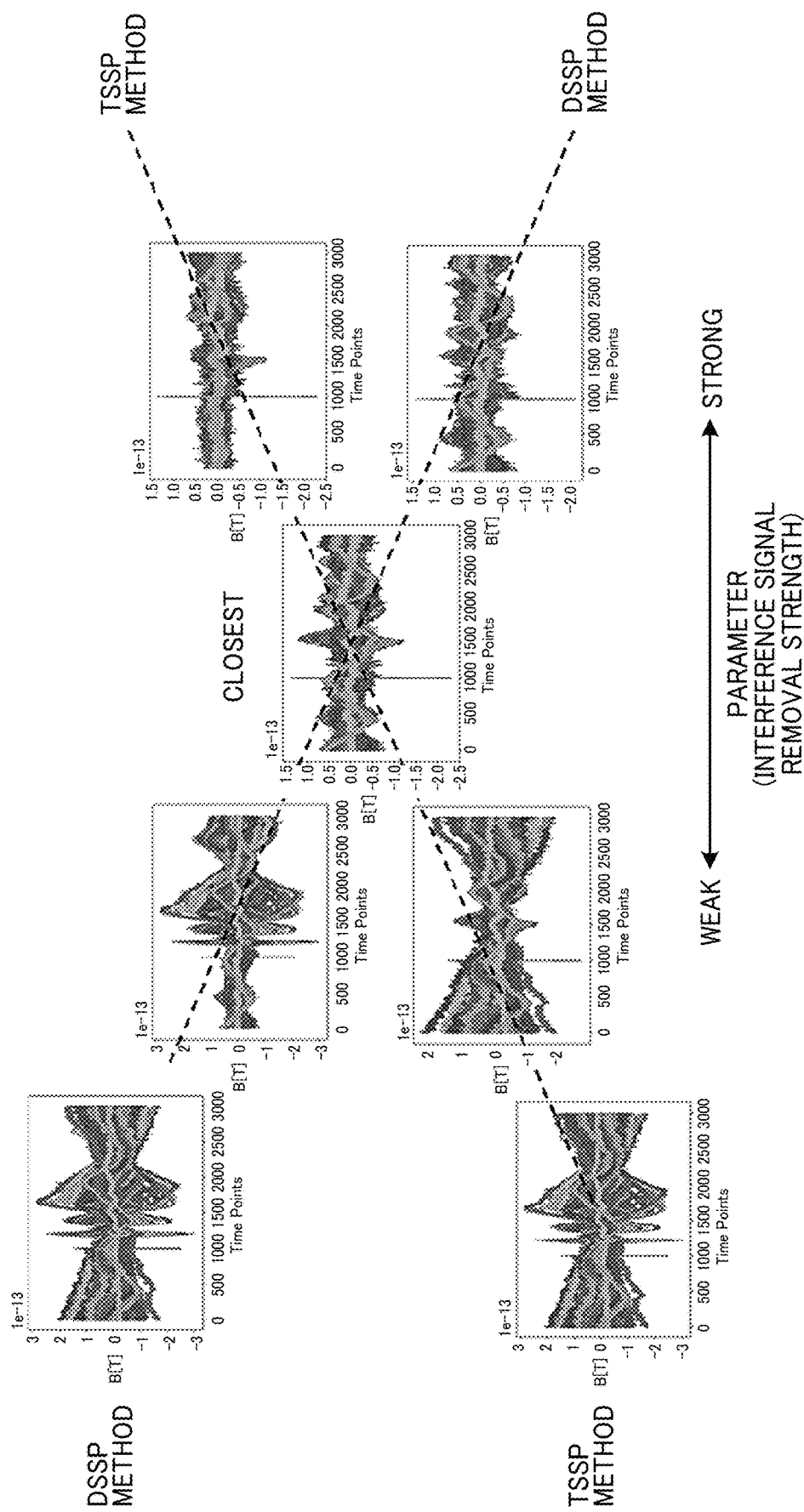
FIG. 5 is a diagram illustrating changes in interference signal removal results when the DSSP method and the TSSP method are used as removal algorithms, according to an embodiment of the present disclosure.

FIG. 5 is a diagram illustrating changes in the interference signal removal results when the DSSP method and the TSSP method are used as the removal algorithms. FIG. 5 schematically illustrates the change in the removal result according to the change of the parameter, when among the two interference signal removal unit 302-1 and 302-2, the interference signal removal unit 302-1 uses the DSSP method and the interference signal removal unit 302-2 uses the TSSP method. The horizontal axis of each graph in FIG. 5 indicates time (1.5 seconds), and the vertical axis indicates magnetic flux density (about 0.5 pT).

Both the DSSP method and the TSSP method have an strength parameter (e.g., "r" in equations (38) and (39) of K. Sekihara, Y. Kawabata, S. Ushio, S. Sumiya, S. Kawabata, Y. Adachi, and S. S. Nagarajan, "Dual signal subspace projection (DSSP): a novel algorithm for removing large interference in biomagnetic measurements", Journal of Neural Engineering, vol. 13, no.3, 036007, 2016) indicating the degree of interference signal removal. However, as illustrated in FIG. 5, between the DSSP method and the TSSP method, the removal result according to the change in the strength parameter represents completely different series. The signal graphs along the broken lines labeled with "DSSP method" and "TSSP method" in FIG. 5 respectively correspond to the removal results using the DSSP method and the TSSP method as the removal algorithms. In both the DSSP method and the TSSP method, the left-end graph represents the original waveform, and signals are gradually removed according to the gradual increase of strength parameter, to reach the right-end waveform. However, in the right-end waveform, a waveform of interest to be measured is also removed together with the interference signals in both the DSSP method and the TSSP method. The optimal value of the strength parameter is to be found and determined before the waveform of interest to be measured is removed as indicated in the right-end waveform.

Comparing the interference signal removal result series between the DSSP method and the TSSP method, there is the closest point where the difference between the two waveforms is the smallest. The closest point is a point where the difference between the interference signal removal results is smaller than a preset value, i.e., a point where the interference signal removal result is within the predetermined error range. Specifically, the closest point is a point where the broken lines intersect, which is labeled as "closest" in FIG. 5.

For example, the interference signal removal result comparator 304 obtains differences between the sensor waveforms for all measurement time points and obtains the sum of the absolute values of the differences for all the sensors, to calculate the difference of the interference signal removal results. Alternatively, the interference signal removal result comparator 304 may obtain correlation coefficient of the waveforms of the same sensor and obtains the sum of the coefficients for all the sensors, calculate the difference of the interference signal removal results. Still alternatively, the interference signal removal result comparator 304 may designate in advance a most desired time point (point of interest) to be observed of signals and performs the above-mentioned difference sum calculation only in the vicinity of the designated time point.

The removal unit 205 outputs the strength parameter and the interference signal removal result at which these two interference signal removal results are closest to each other, i.e., the sensor signals from which the interference signals are removed are within the predetermined error range as the optimal parameter and the interference signal removal result, respectively. For example, the removal unit 205 adopts the average value of the sensor waveforms as a final result of removing the interference signal. Alternatively, the removal unit 205 can determine in advance the priority among the interference signal removal units 302-1 to 302-$n$, and adopts the interference signal removal result having the highest priority.

Further, when the interference signal removal result comparator 304 selects any removal algorithm other than the DSSP method and the TSSP method, the processing is performed in substantially the same manner. In other words, the interference signal removal result comparator 304 compares the waveforms output from corresponding sensors. Further, the interference signal removal result comparator 304 obtains the interference signal removal result in which the point at which the waveforms outputs from the corresponding sensors are closest, i.e., the sensor signals from which the interference signals are removed is within the predetermined error range, and the parameter used in the removal algorithm when such interference signal removal result is obtained.

In view of the way of obtaining the closest point as described above, a set of algorithms in which changes in the removal result according to the change of the parameter appear as different series (the changes in the removal result are different from each other) is suitable as the removal algorithms used in the interference signal removal unit 302-1 to 302-$n$.

Further, the above described configuration and method apply to a case in which three or more interference signal removal units are provided. In this case, the interference signal removal result may be compared in a "majority decision" manner. In other words, in a configuration having three interference signal removal units 302-1 to 302-3 using the three removal algorithms A, B, and C respectively, the differences between the interference signal removal results obtained by any two algorithms among the three algorithms at the closest point is obtained.

Specifically, the difference of the interference signal removal results between the interference signal removal units 302-1 and 302-2 at the closest point is diff(1−2). Further, the difference of the interference signal removal results between the interference signal removal units 302-2 and 302-3 at the closest point is diff(2−3). Furthermore, the difference of the interference signal removal results between the interference signal removal units 302-3 and 302-1 at the closest point is diff(3−1).

For example, when diff(1−2)«diff(2−3) and diff(1−2)«diff(3−1), it means that the difference of the result obtained by the interference signal removal unit 302-3, which uses the removal algorithm C, is larger than the result of the interference signal removal units 302-1 and 302-2, which use the removal algorithms A and B, respectively.

In this case, the interference signal removal result comparator 304 adopts the results of the interference signal removal unit 302-1 and the interference signal removal unit 302-2 as the result of the interference signal removal, and ignores the result of the interference signal removal unit 302-3. In other words, the interference signal removal result comparator 304 regards the result of the interference signal removal unit 302-3 as if it was not obtained in the first place. In substantially the same manner, four or more interference signal removal units 302-1 to 302-$n$ (n4) are provided, the interference signal removal result comparator 304 adopts the result obtained by the two interference signal removal units by which the small difference between the interference signal removal results is obtained, and does not adopt the result obtained by the interference signal removal unit by which a large difference is obtained.

Operation of Removing Interference Signal

Figure 6:
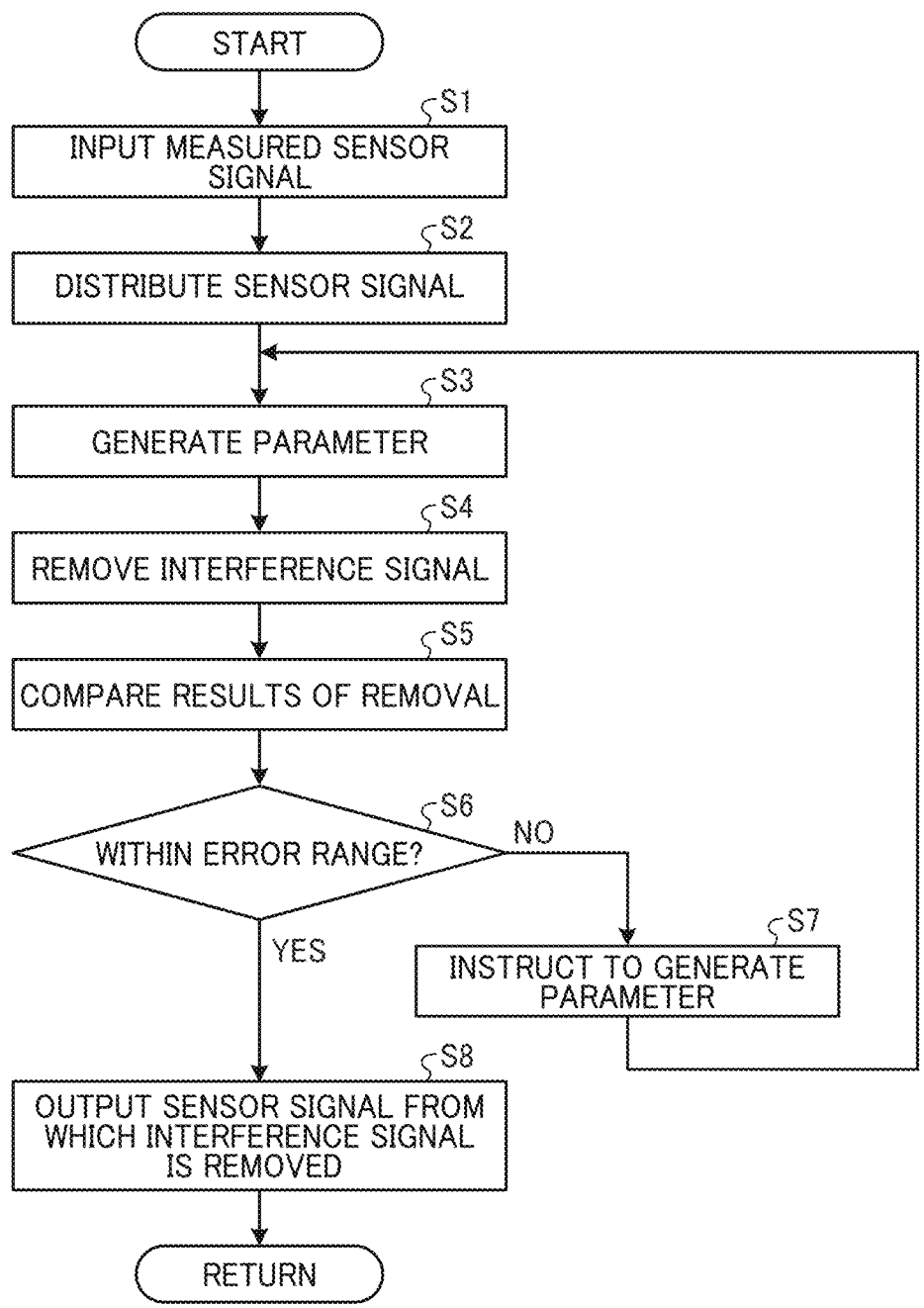
FIG. 6 is a flowchart illustrating an example of processes in operation of removing interference signals, according to an embodiment of the present disclosure.

Operation of removing interference signals performed by the removal unit 205 is described hereinafter with reference to FIG. 6. FIG. 6 is a flowchart illustrating an example of processes in operation of removing interference signals.

The measurement signal input unit 301 of the removal unit 205 receives an input of time-series sensor signals (measured sensor signals) of multiple channels (step S1). Further the measurement signal input unit 301 distribute the received sensor signals (step S2), to send the received signals to each of the interference signal removal unit 302-1 to 302-$n$.

The interference signal removal parameter generator 303 generates parameters unique to the plurality of removal algorithms used by the interference signal removal units 302-1 to 302-n respectively (step S3), and sends the generated parameters to the interference signal removal unit 302-1 to 302-n.

The interference signal removal unit 302-1 to 302-n applies the parameters generated by the interference signal removal parameter generator 303 to the removal algorithms, to remove the interference signals from the measured sensor signals (step S4).

The interference signal removal result comparator 304 compares the sensor signals from which the interference signals are removed by the interference signal removal units 302-1 to 302-n (step S5). Then, the interference signal removal result comparator 304 determines whether the sensor signals from which the interference signals are removed are within the predetermined error range (step S6).

When the sensor signals from which the interference signals are removed are within the predetermined error range (step S6: Yes), the interference signal removal result comparator 304 determines the parameter of each of the plurality of removal algorithms used in this interference signal removal process as the parameter of each the plurality of removal algorithms. Then, the interference signal removal result comparator 304 outputs, to extraneous sources, the interference signal removal result, and the parameters P1 to Pn used by the interference signal removal units 302-1 to 302-n in this interference signal removal process (step S8).

By contrast, when the sensor signals from which the interference signals are removed are out of the predetermined error range (step S6: No), the interference signal removal result comparator 304 instructs the interference signal removal parameter generator 303 to generate a parameter (step S7). In this process, the interference signal removal result comparator 304 instructs the interference signal removal parameter generator 303 to generate a parameter of each of the plurality of removal algorithms and output each generated parameter to each of the interference signal removal units 302-1 to 302-n. The operation returns to step S3, and the removal unit 205 repeats the processes of step S3 and subsequent steps. The removal unit 205 repeats the processes of steps S7 and S3 to S5 until the sensor signals from which the interference signals are removed fall within the predetermined error range.

As described heretofore, in the information processing apparatus 50 (information display apparatus) according to the first embodiment, the interference signal removal result comparator 304 of the removal unit 205 determines the parameter of the signal separation algorithm that separates the signal of interest from the mixed signals in which signals emitted from a plurality of signal sources are mixed. Further, the interference signal removal result comparator 304 compares signal separation results by the plurality of signal separation algorithms performed on the mixed signals, to determine the parameter of each the plurality of signal separation algorithms.

In the example of the first embodiment, the interference signal removal result comparator 304 determines the parameter of the signal separation algorithm (removal algorithm) that removes interference magnetic field signals from biomagnetism measurement signals (sensor signals) measured by the plurality of sensors and separates the signals obtained by removing the interference magnetic field signals. In this configuration and process, the interference signal removal result comparator 304 compares the signal separation results obtained by the plurality of removal algorithms performed on the sensor signals, to determine the parameter of each of the plurality of signal separation algorithms. In other words, the removal unit 205 according to the first embodiment performs a plurality of different removal algorithms on the sensor signals measured by the plurality of sensors, and directly compares the signal separation results, to determine the parameter of each of the plurality of the removal algorithms.

Therefore, the removal unit 205 according to the first embodiment obtains the parameter even when the sensor signals include no characteristic spike wave. Further, the removal unit 205 does not have to use EEG signals measured at the same time. Therefore, the removal unit 205 according to the first embodiment automatically derives a parameter applicable not only to magneto-encephalography measurement of epilepsy patients, but also to removal of interference magnetic fields in biomagnetism measurements of other cases or sites. In other words, the parameter determination according to the first embodiment is applicable to magnetic field measurement caused by activity of other sites such as a spine, heart, or muscle, or to magnetic field measurement for other cases. Thus, the parameters of the interference magnetic field removal algorithms are automatically derived, thereby implementing more effective measurement of the biometric magnetic field.

Therefore, according to the first embodiment, the optimal parameters of the signal separation algorithms for separating the signal of interest from the mixed signals are derived. The technique of detecting spike waves and performing the ECD estimation is applicable only to magneto-encephalography measurement of epilepsy patients in which characteristic spike waves appear. Further, the technique requires electroencephalography data measured simultaneously in order to detect spikes. Accordingly, the convenience of magneto-encephalography measurement degrades. In the first place, the above technique is limited to magneto-encephalography measurement because the technique uses the ECD estimation. For this reason, it is difficult to apply the above technique to measurement of a magnetic field caused by the activity of other parts such as a spine, heart, or muscle.

According to an embodiment, an optimal parameter of signal separation algorithm used in separating a signal of interest from a mixed signal, which is a measurement result of the biomagnetism measurement, is derived.

The above-described embodiments are illustrative and do not limit the present disclosure. Thus, numerous additional modifications and variations are possible in light of the above teachings. For example, elements and/or features of different illustrative embodiments may be combined with each other and/or substituted for each other within the scope of the present disclosure.

Any one of the above-described operations may be performed in various other ways, for example, in an order different from the one described above.

Each of the functions of the described embodiments can be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. A determination apparatus comprising:
 a sensor to detect signals and which outputs a mixed signal which has been detected including biomedical signals from a subject and an interference signal;

circuitry configured to:
  compare signal separation results obtained by a plurality of signal separation algorithms including two or more algorithms from a group including a dual signal subspace projection ("DSSP") method, a temporally extended signal space separation ("tSSS") method, and principal component analysis (PCA)/independent component analysis (ICA) executed on the mixed signal in which signals emitted from a plurality of signal sources are mixed, each of the plurality of signal separation algorithms being an algorithm separating a signal of interest from the mixed signal; and
  determine a parameter of each of the plurality of signal separation algorithms based on a comparison result,
wherein the circuitry determines the parameter of each of the plurality of signal separation algorithms at which each of the signal separation results is within a predetermined error range as the parameter of each of the plurality of signal separation algorithms.

2. The determination apparatus of claim 1, wherein:
the circuitry is further configured to output each of the signal separation results when each of the signal separation results is within the predetermined error range.

3. The determination apparatus of claim 1, wherein the circuitry is further configured to:
  generate the parameter of each of the plurality of signal separation algorithms;
  perform signal separation using any two or more signal separation algorithms of the plurality of signal separation algorithms using a particular parameter corresponding to each of the two or more signal separation algorithms among the generated parameters;
  when each of the signal separation results is out of the predetermined error range, generate a new parameter of each of the plurality of signal separation algorithms; and
  output the generated new parameter of each of the plurality of signal separation algorithms.

4. The determination apparatus of claim 3, wherein:
the circuitry removes an interference magnetic field signal included in the interference signal from the mixed signal measured in biomagnetism measurement using any of the plurality of signal separation algorithms, and separates a signal obtained by removing the interference magnetic field signal as the signal of interest.

5. A biomagnetism measuring apparatus comprising:
a sensor to detect signals and which outputs a mixed signal which has been detected including biomedical signals from a subject and an interference signal:
circuitry configured to:
  compare signal separation results obtained by a plurality of signal separation algorithms including two or more algorithms from a group including a dual signal subspace projection ("DSSP") method, a temporally extended signal space separation ("tSSS") method, and principal component analysis (PCA)/independent component analysis (ICA) executed on biomagnetism measurement signals measured by a plurality of sensors, each of the plurality of signal separation algorithms being an algorithm removing an interference magnetic field signal from the biomagnetism measurement signals; and
  determine a parameter of each of the plurality of signal separation algorithms based on a comparison result,
wherein the circuitry determines the parameter of each of the plurality of signal separation algorithms at which each of the signal separation results is within a predetermined error range as the parameter of each of the plurality of signal separation algorithms.

6. The biomagnetism measuring apparatus of claim 5, wherein:
the circuitry is further configured to output each of the signal separation results when each of the signal separation results is within the predetermined error range.

7. The biomagnetism measuring apparatus of claim 5, wherein the circuitry is further configured to:
  generate the parameter of each of the plurality of signal separation algorithms;
  perform signal separation using any two or more signal separation algorithms of the plurality of signal separation algorithms using a particular parameter corresponding to each of the two or more signal separation algorithms among the generated parameters;
  when each of the signal separation results is out of the predetermined error range, generate a new parameter of each of the plurality of signal separation algorithms; and
  output the generated new parameter of each of the plurality of signal separation algorithms.

8. The biomagnetism measuring apparatus of claim 7, wherein:
the circuitry removes an interference magnetic field signal included in the interference signal from the mixed signal measured in biomagnetism measurement using any of the plurality of signal separation algorithms, and separates a signal obtained by removing the interference magnetic field signal as a signal of interest.

9. A method, comprising:
detecting signals and outputting a mixed signal including biomedical signals from a subject and an interference signal;
comparing signal separation results obtained by a plurality of signal separation algorithms including two or more algorithms from a group including a dual signal subspace projection ("DSSP") method, a temporally extended signal space separation ("tSSS") method, and principal component analysis (PCA)/independent component analysis (ICA executed on the mixed signal; and
determining a parameter of each of the plurality of signal separation algorithms based on a comparison result, the determining determines the parameter of each of the plurality of signal separation algorithms at which each of the signal separation results is within a predetermined error range as the parameter of each of the plurality of signal separation algorithms.

10. The method of claim 9, further comprising:
outputting each of the signal separation results when each of the signal separation results is within the predetermined error range.

11. The method of claim 9, further comprising:
  generating the parameter of each of the plurality of signal separation algorithms;
  performing signal separation using any two or more signal separation algorithms of the plurality of signal separation algorithms using a particular parameter corresponding to each of the two or more signal separation algorithms among the generated parameters;
  when each of the signal separation results is out of the predetermined error range, generating a new parameter of each of the plurality of signal separation algorithms; and
  outputting the generated new parameter of each of the plurality of signal separation algorithms.

12. The method of claim 11, further comprising:
removing an interference magnetic field signal included in the interference signal using any of the plurality of signal separation algorithms, and separating a signal obtained by removing the interference magnetic field signal as a signal of interest.

\* \* \* \* \*